(12) United States Patent
Beacham et al.

(10) Patent No.: US 11,446,002 B2
(45) Date of Patent: Sep. 20, 2022

(54) METHODS AND SYSTEMS FOR A MEDICAL IMAGING DEVICE

(71) Applicant: GE Precision Healthcare LLC, Milwaukee, WI (US)

(72) Inventors: Jimmie Autrey Beacham, West Allis, WI (US); Andrew Jungwirth, Eagle, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 142 days.

(21) Appl. No.: 16/575,284

(22) Filed: Sep. 18, 2019

(65) Prior Publication Data

US 2021/0077069 A1 Mar. 18, 2021

(51) Int. Cl.
| | | |
|---|---|---|
| *A61B 8/00* | (2006.01) | |
| *G01N 29/265* | (2006.01) | |
| *G01N 29/22* | (2006.01) | |
| *A61B 8/14* | (2006.01) | |
| *A61B 8/08* | (2006.01) | |
| *A61B 34/30* | (2016.01) | |

(52) U.S. Cl.
CPC ............ *A61B 8/4218* (2013.01); *A61B 8/085* (2013.01); *A61B 8/0875* (2013.01); *A61B 8/0891* (2013.01); *A61B 8/145* (2013.01); *A61B 8/4254* (2013.01); *A61B 8/4455* (2013.01); *A61B 8/54* (2013.01); *G01N 29/226* (2013.01); *G01N 29/265* (2013.01); *A61B 34/30* (2016.02)

(58) Field of Classification Search
CPC ..... A61B 8/4218; A61B 8/4254; A61B 8/145; A61B 8/0891; A61B 8/0875; A61B 8/085; A61B 8/4455; A61B 8/54; A61B 34/30; G01N 29/265; G01N 29/226
See application file for complete search history.

(56) References Cited

U.S. PATENT DOCUMENTS

| | | | |
|---|---|---|---|
| 6,425,865 B1 * | 7/2002 | Salcudean ............ | A61B 8/0875 600/111 |
| 2006/0142657 A1 * | 6/2006 | Quaid ................... | A61B 34/76 600/424 |
| 2009/0036902 A1 * | 2/2009 | DiMaio ................. | A61B 34/30 606/130 |
| 2014/0121520 A1 * | 5/2014 | Wang .................... | A61B 8/403 600/444 |
| 2015/0196802 A1 * | 7/2015 | Siegel ................ | A63B 21/0023 482/8 |
| 2016/0206291 A1 * | 7/2016 | Yang .................... | A61B 8/5253 |
| 2017/0326734 A1 * | 11/2017 | Iida ....................... | B25J 9/1674 |
| 2020/0113542 A1 * | 4/2020 | Perrey .................. | A61B 34/20 |
| 2021/0031385 A1 * | 2/2021 | Rembisz ................ | G01S 17/42 |

* cited by examiner

*Primary Examiner* — Joseph M Santos Rodriguez
*Assistant Examiner* — Kaitlyn E Sebastian
(74) *Attorney, Agent, or Firm* — McCoy Russell LLP (57) ABSTRACT

Various systems are provided for an ultrasound imaging system. In one example, a method comprises learning a travel path profile and one or more pressures applied along the travel path profile in response to an external handle force and acquiring an ultrasound image along the travel path profile by applying one or more pressures against an acquisition surface of a patient via a robot without the external handle force.

18 Claims, 7 Drawing Sheets

METHODS AND SYSTEMS FOR A MEDICAL IMAGING DEVICE

TECHNICAL FIELD

Embodiments of the subject matter disclosed herein relate to medical imaging and the facilitation of ultrasonic tissue scanning.

DISCUSSION OF ART

In ultrasonic diagnostic apparatuses, ultrasound is transmitted from an ultrasonic probe to the inside of a subject, and echo signals reflected from the inside of the subject are received by the ultrasonic probe. Then, an ultrasonic image is produced based on the received echo signals and displayed on a display device.

BRIEF DESCRIPTION

In one embodiment, a method comprises learning a travel path profile and one or more pressures applied along the travel path profile in response to an external handle force and acquiring an ultrasound image along the travel path profile by applying one or more pressures against an acquisition surface of a patient via a robot without the external handle force.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1A:
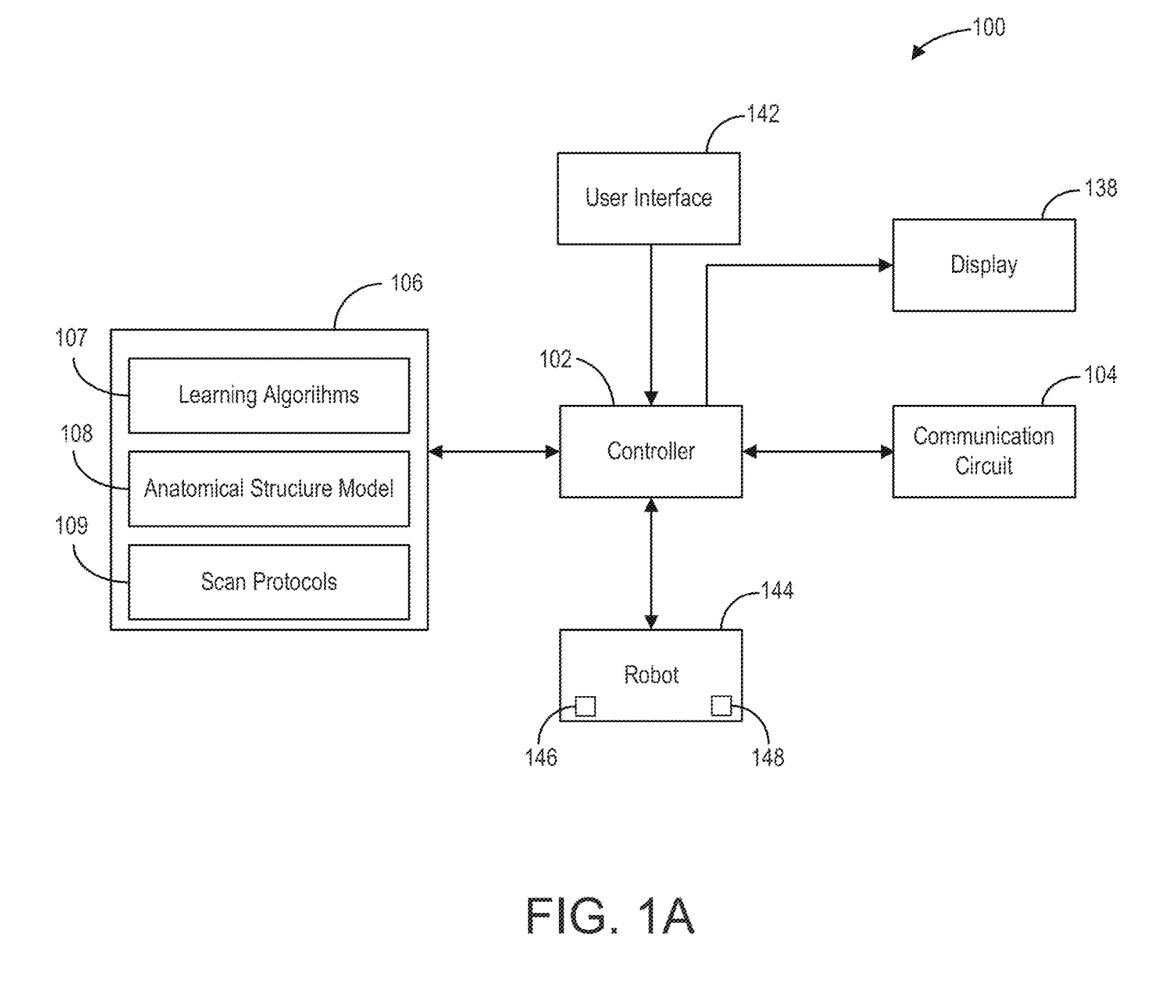
FIGS. 1A-1B show schematic diagrams of medical diagnostic systems, according to embodiments of the disclosure.
Figure 1B:
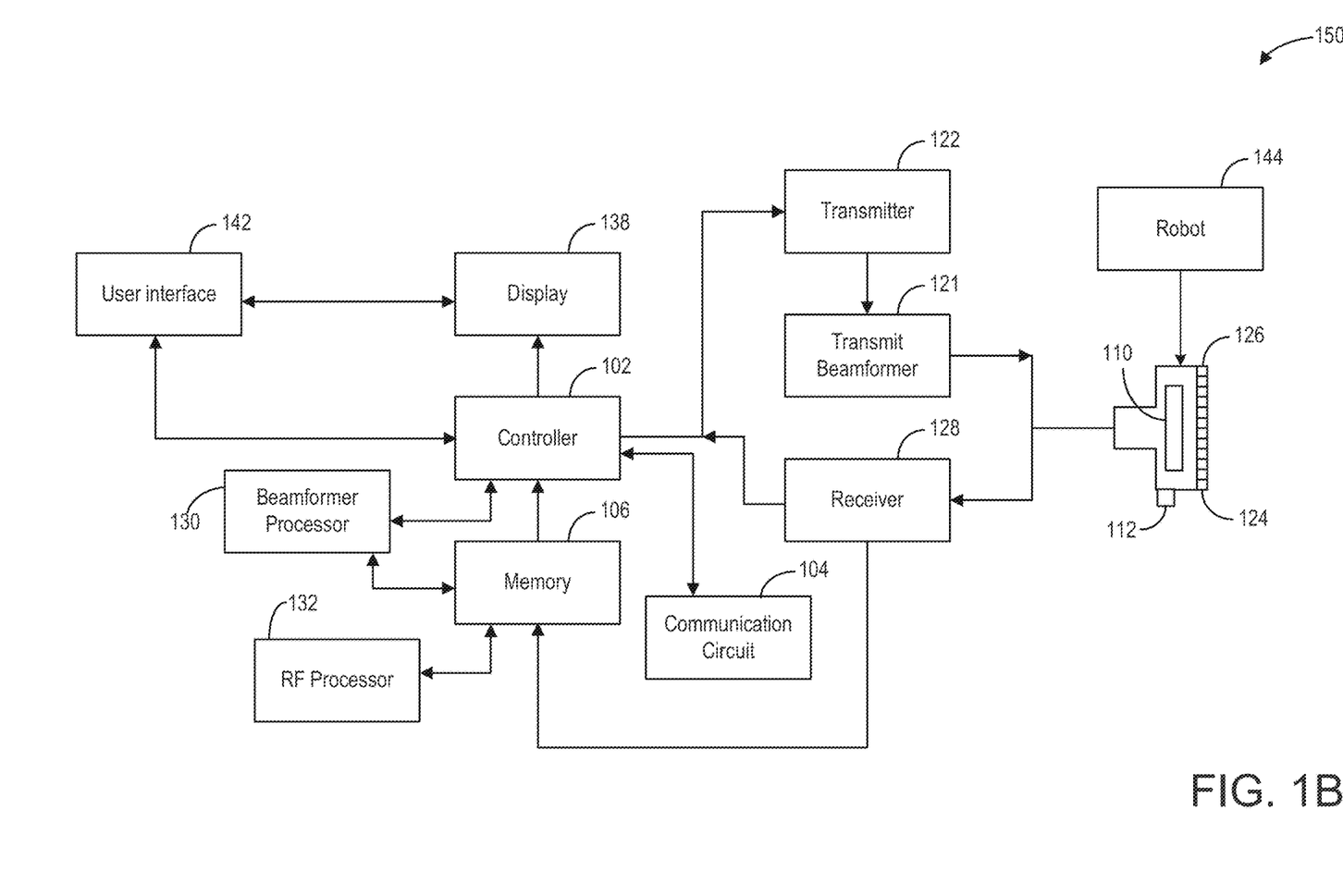
Figure 2A:
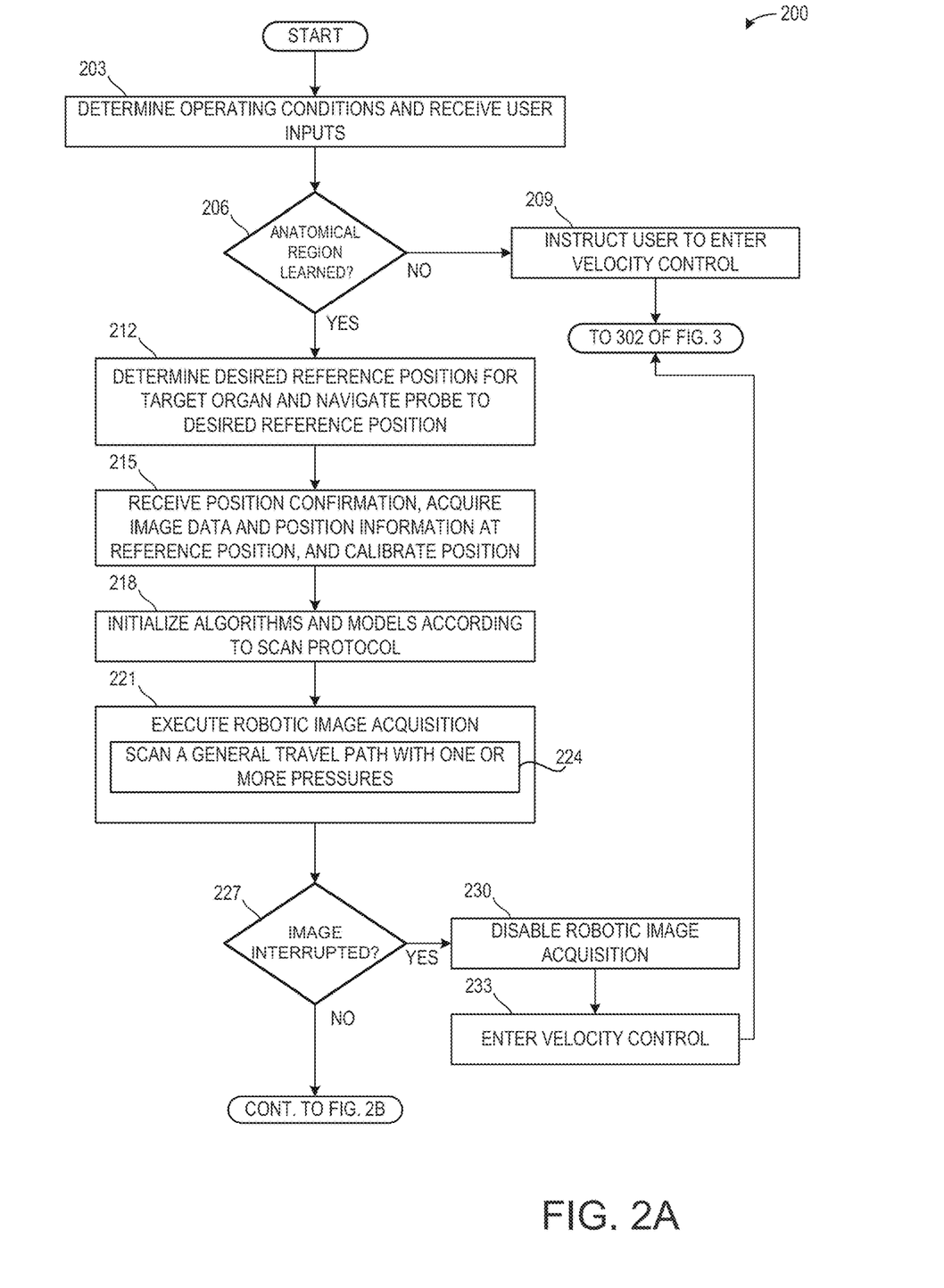
FIGS. 2A and 2B show a method for acquiring an ultrasound image via a robot or a user.
Figure 2B:
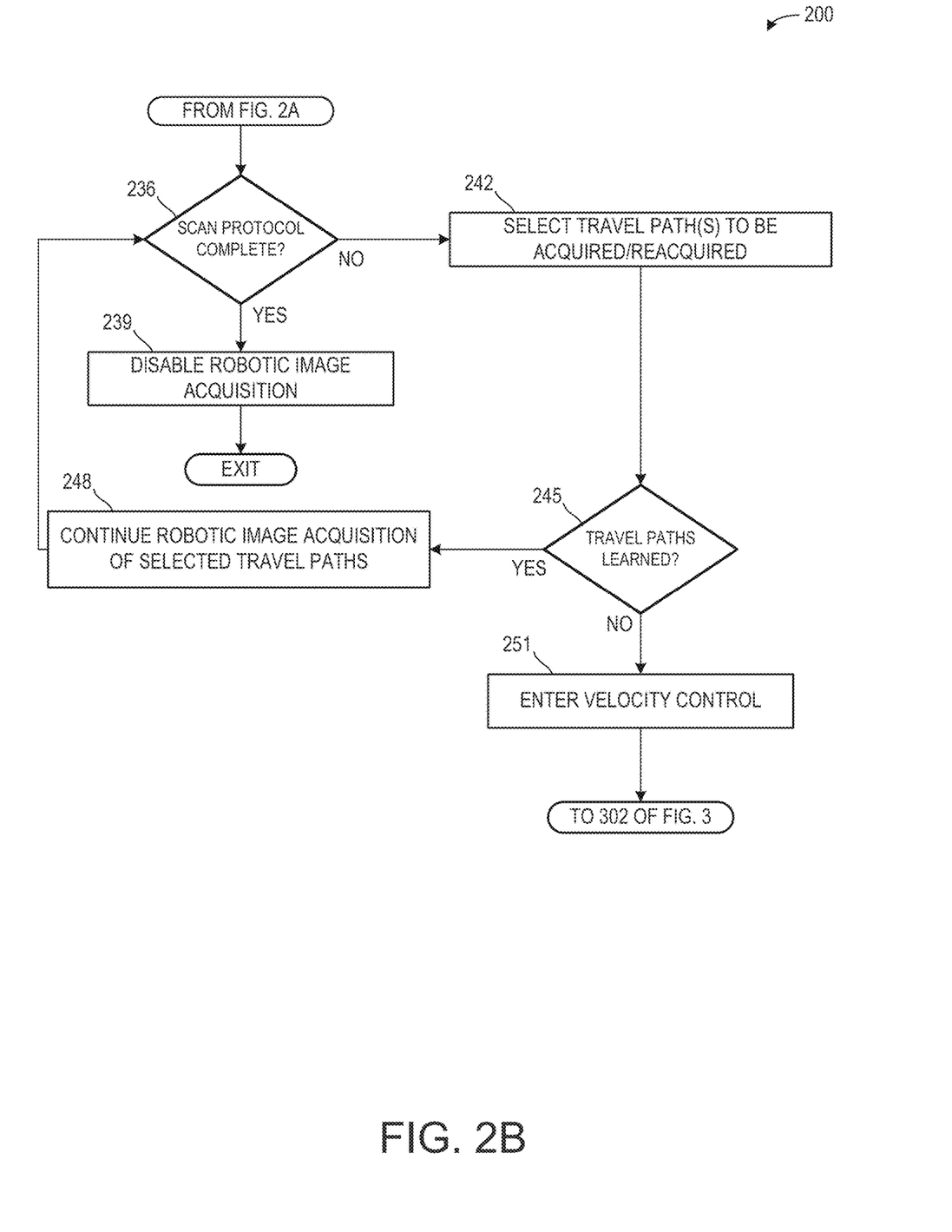
Figure 3:
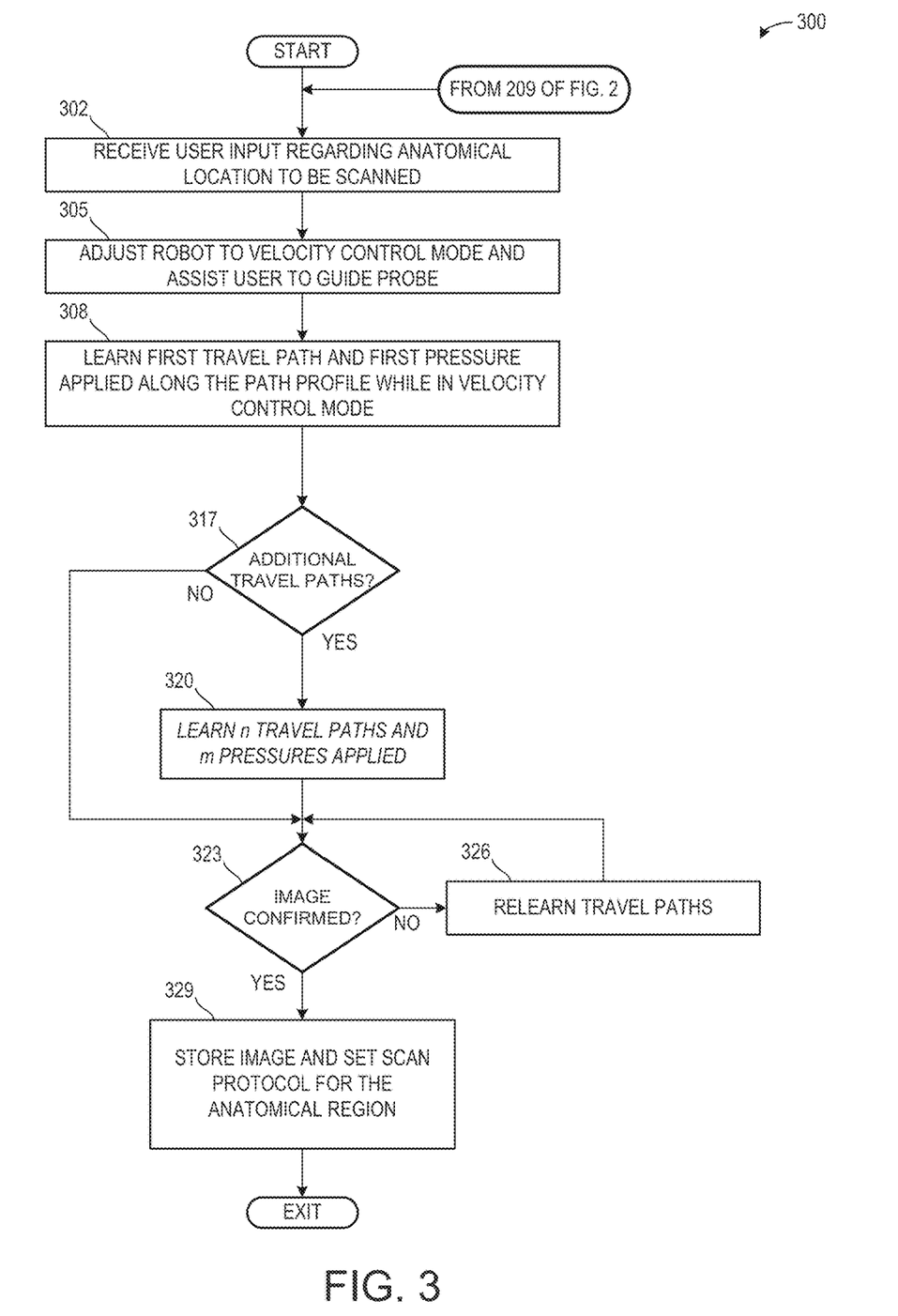
FIG. 3 shows a method for teaching the robot a travel path profile for a scan protocol.
Figure 4A:
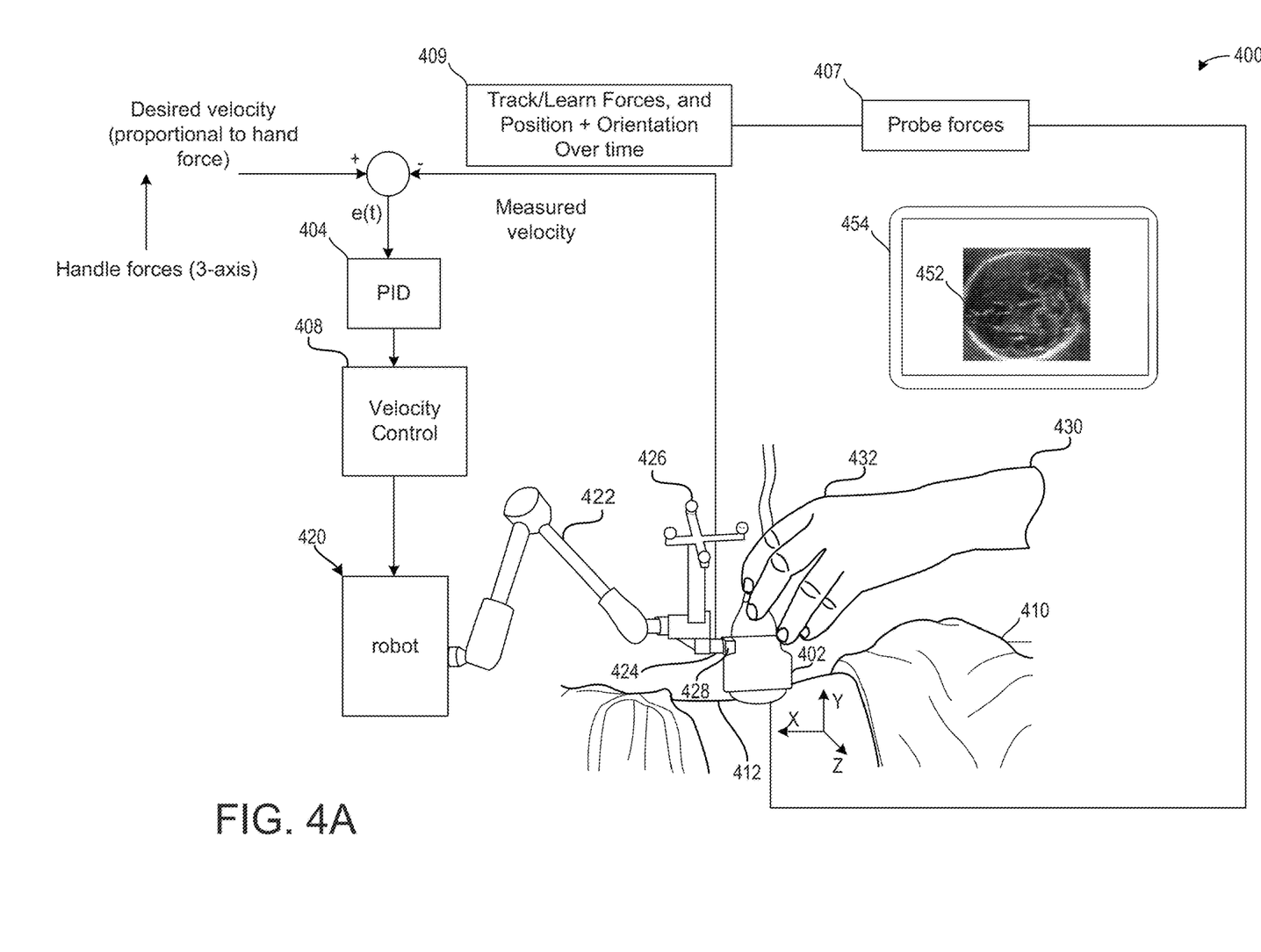
FIG. 4A shows an embodiment where the robot is learning a travel path based on a plurality of user forces.
Figure 4B:
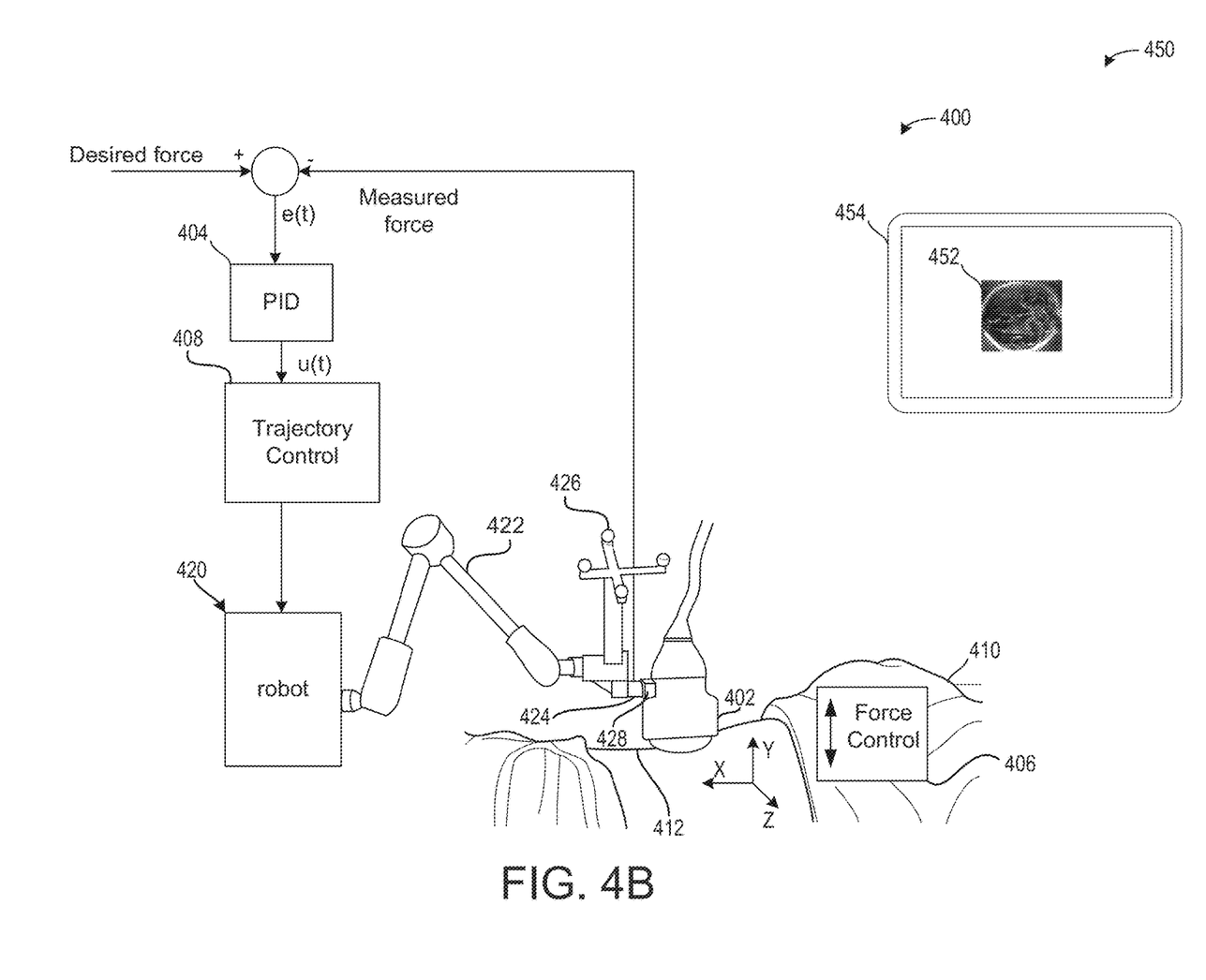
FIG. 4B shows an embodiment where the robot is acquiring an ultrasound image along a learned travel path without an external force present.

The following description relates to embodiments of a robot configured to actuate an ultrasound probe of an ultrasound image system to acquire an ultrasound image corresponding to a desired scan protocol. An example of the ultrasound image system is shown in FIGS. 1A and 1B. FIGS. 2A and 2B illustrate a method for acquiring an ultrasound image via either the robot or a user, wherein the robot may be selected to acquire the ultrasound image if the robot has learned the travel path profile. The robot may be configured to learn a travel path profile, wherein the travel path profile comprises velocities parallel to an acquisition surface, forces angled to the acquisition surfaces, and various probe orientations. A method for learning at least one travel path and various forces, velocities, and orientations applied along the travel path is illustrated in FIG. 3. A schematic of the robot in combination with a plurality of sensors and actuators is illustrated in FIG. 4A. Therein, a user guides the ultrasound probe, to which an arm of the robot is coupled, and guides the probe along a travel path. The robot senses forces applied by the user directly to the probe handle and to an acquisition surface via the ultrasound probe. The robot may estimate a velocity via the probe handle force and a probe force with which to apply to the acquisition surface via measuring an amount of motor actuation in combination with a sensed probe force. FIG. 4B illustrates the robot acquiring the ultrasound image as it actuates the ultrasound probe across the acquisition surface in response to ultrasound probe being free of an external force, such as a handle force applied by the user.

FIGS. 1A-1B illustrate schematic block diagrams of first and second embodiments of a medical diagnostic system (MDS) 100, 150, respectively. The MDS 100 of FIG. 1A includes a controller (e.g., controller circuit) 102 operably coupled to a communication circuit 104, a display (e.g., display device) 138, a user interface 142, a robot 144, and a memory 106.

The communication circuit 104 may be communicatively coupled to one or more additional MDS (e.g., such as the MDS 150 shown in FIG. 1B), one or more medical diagnostic imaging devices, a remote server, and/or the like via corresponding bi-directional communication links. The one or more medical diagnostic imaging systems may include ultrasound imaging systems or devices, in one example. The remote server may be configured to store sets of medical images from prior scanning and/or clinician sessions of a patient acquired by the one or more medical diagnostic imaging systems.

The bi-directional communication links may be a wired (e.g., via a physical conductor) and/or wireless communication (e.g., utilizing radio frequency (RF)) link for exchanging data (e.g., data packets) between the MDS 100 and the alternative MDS, the one or more medical diagnostic imaging systems, the remote server, and/or the like. For example, the MDS 100 may receive a set of medical images from saved scanning and/or clinician sessions from the alternative MDS, the one or more medical diagnostic imaging systems, the remote server, and/or the like. The set of medical images may include medical imaging data used to generate the images and corresponding position sensor data from a probe used to acquire the medical imaging data, as discussed further herein. The bi-directional communication links may be based on a standard communication protocol, such as Ethernet, transmission control protocol/internet protocol (TCP/IP), WiFi, 802.11, a customized communication protocol, and/or the like.

The controller 102 is configured to control the operation of the MDS 100. The controller 102 may include one or more processors. Optionally, the controller 102 may include a central processing unit (CPU), one or more microprocessors, a graphics processing unit (GPU), or other electronic components capable of processing inputted data according to specific logical instructions stored on a memory of the controller or coupled with the controller. Optionally, the controller 102 may include and/or represent one or more hardware circuits or circuitry that include, are connected with, or that both include and are connected with one or more processors, controllers, and/or other hardware logicbased devices. Additionally or alternatively, the controller 102 may execute instructions stored on a tangible and non-transitory computer readable medium (e.g., the memory 106).

The controller 102 may be operably coupled to and/or control the communication circuit 104. The communication circuit 104 is configured to receive and/or transmit information with the one or more medical diagnostic imaging systems, the alternative MDS, the remote server, and/or the like. The communication circuit 104 may represent hardware that is used to transmit and/or receive data along the bi-directional communication links. The communication circuit 104 may include a transceiver, receiver, etc., and associated circuitry (e.g., antennas) for wired and/or wirelessly communicating (e.g., transmitting and/or receiving) with the one or more medical diagnostic imaging systems, the alternative MDS, the remote server, and/or the like. For example, protocol firmware may be stored in the memory 106, which is accessed by the controller 102. The protocol firmware provides the network protocol syntax for the controller 102 to assemble data packets, establish and/or partition data received along the bi-directional communication links, and/or the like.

The controller 102 is operably coupled to the display 138 and the user interface 142. The display 138 may include one or more liquid crystal displays (e.g., light emitting diode (LED) backlight), organic light emitting diode (OLED) displays, plasma displays, cathode ray tube (CRT) displays, and/or the like. The display 138 may display patient information, one or more medical images and/or videos, components of a graphical user interface, one or more 2D, 3D, or 4D ultrasound image data sets from ultrasound data stored in the memory 106 or currently being acquired, measurements, diagnosis, treatment information, alerts or indications, directions, and/or the like received by the display 138 from the controller circuit 102.

The user interface 142 controls operations of the controller 102 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142. For example, a portion of the user interface 142 may correspond to a graphical user interface (GUI) generated by the controller 102, which is shown on the display 138. The touch screen display can detect a presence of a touch from the operator on the display 138 and can also identify a location of the touch with respect to a surface area of the display 138. For example, the user may select one or more user interface icons of the GUI shown on the display by touching or making contact with the display 138. The touch may be applied by, for example, at least one of an individual's hand, glove, stylus, or the like.

The memory 106 includes instructions, parameters, algorithms, models, data values, and/or the like utilized by the controller 102 to perform one or more operations described herein. The memory 106 may be a tangible and non-transitory computer readable medium such as flash memory, random access memory (RAMI, read-only memory (ROM), electrically erasable programmable read-only memory (EE-PROM), and/or the like. The memory 106 may include a set of machine learning algorithms 107 (e.g., convolutional neural network algorithms, deep learning algorithms, decision tree learning algorithms, and/or the like) configured to define a plurality of models 109 and an anatomical structure model 108. Additionally or alternatively, the models 109 and/or the anatomical structure model 108 may be received along one of the bi-directional communication links via the communication circuit 104 and stored in the memory 106.

For example, the anatomical structure model 108 may be defined by the machine learning algorithms 107 to identify one or more anatomical structures of interest (e.g., reference points) based on features of the one or more anatomical structures (e.g., boundaries, thickness, and/or the like) within the one or more medical images. The features may represent high level features of the pixels and/or voxels of the medical image such as a histogram orient gradients, blob features, covariance features, binary pattern features, and/or the like. Optionally, the machine learning algorithm 107 may define the anatomical structure model 108 by automatically building a statistical model and/or a database of true positives and true negatives corresponding to each anatomical structure identified based on the features from a set of training images, a classification model, supervised modeling, and/or the like.

For example, the anatomical structure model 108 may be configured and/or designed based on a plurality of training medical images and/or a plurality of scan protocols. The plurality of scan protocols may be grouped into different anatomical structure sets, such as organs (e.g., heart, kidney, liver, bladder, lung, brain, and/or the like), skeletal structures (e.g., bone, skull, and/or the like), vascular structures (e.g., artery, vein, and/or the like), regions of a body (e.g., head, torso, and/or the like), and/or the like.

Additionally or alternatively, the anatomical structure model 108 may be defined based on a supervised learning method. For example, a user (e.g., skilled medical practitioner) may manually label the one or more anatomical structures within the plurality of training medical images utilizing the user interface 142 and an ultrasound probe (e.g., ultrasound probe 126 of FIG. 1B) and the robot 144. The manually labeled medical images may be used to build a statistical model and/or a database of true positives and true negatives corresponding to each anatomical structure defining the anatomical structure model 108.

The plurality of scan protocols 109 are configured to define a sequence of scans to generate a desired ultrasound image. The desired ultrasound image may comprise a plurality of ultrasound images combined to produce a three-dimensional view of an anatomical region. Each scan protocol of the plurality of scan protocols 109 may comprise one or more travel paths along with one or more forces. The one or more forces comprise at least a probe force and/or an interface force, which may correspond to a force at which the probe is pressed against an acquisition surface (e.g., a patient's skin). The probe force may occur at a plurality of angles relative to the acquisition surface, wherein the plurality of angles may also be stored with a corresponding travel path profile of a single scan protocol. The travel path profile may further comprise a velocity at which to move the ultrasound probe along the travel path. The entirety of the scan protocol may be learned via the robot 144. In one example, the robot 144 is a collaborative robot.

For example, if the desired anatomical region is the head, then the robot 144 may learn to scan structures within the head, wherein features of the head (e.g., eye socket, internal bone structure, thickness, shape, and/or the like) are identified within the medical image as a check to ensure the robot 144 is correctly traveling along the travel path. The features may be based on high level features of the pixels and/or voxels of the medical image such as a histogram orient gradients, blob features, covariance features, binary pattern features, and/or the like.

In one embodiment, the user may actuate a probe (e.g., probe 126 of FIG. 1B), to which an arm of the robot 144 may be coupled. As the probe is actuated, memory 106 may be updated, including the learning algorithms, the anatomical structure model 108, and the scan protocols 109. Specifically, the scan protocols 109 may comprise a plurality of travel path profiles, each corresponding to an ultrasound scan sequence for a specific anatomical region or an ultrasound scan type (e.g., fetal scan type, kidney scan type, etc.). Each travel path profile may comprise a set of forces and a set of positions at which to apply one or more forces at one or more angles. Each travel path profile may further comprise a velocity at which it is desired for the robot 144 to actuate the ultrasound probe along the travel path. The robot 144 may comprise a plurality of sensor 146 and actuators 148, which may provide feedback a force of movement of an appendage of the robot 144 along with other feedback.

In this way, the learning algorithms 107, anatomical structure model 108, and scan protocols 109 may together form instructions executed by the controller 102 and signaled to the robot 144 to acquire an ultrasound image with inputs from a user. The images and/or image data may be classified by scan plane of an anatomical structure and/or by anatomical landmark/structure such that a target or desired scan plane or anatomical structure is identified by the controller, using the stored models and/or algorithms. The identified target scan plane(s) of an anatomical structure and/or an anatomical structure may then be displayed to a user via the display 138. In this way, the user may be able to visualize in real-time if the robot 144 is accurately acquiring a desired ultrasound image. Furthermore, the identification of the various landmarks and/or structures (e.g., reference points) may enable the controller to adjust an operation of the robot 144 (e.g., a force applied to the acquisition surface and/or an orientation of the probe relative to the acquisition surface) in response to a currently acquired image not matching a previously acquired image. Such a mismatch may occur due to variability between patients due to height, weight, and other differences. However, by allowing the robot 144 to follow a general learned travel path, a direction, length, and location of the travel path may be substantially similar across a broad spectrum of patients.

Turning to FIG. 1B, the MDS 150 may be integrated with and/or a part of a medical diagnostic imaging system. For example, the MDS 150 includes an ultrasound imaging system. The MDS 150 includes an ultrasound probe 126 having a transmitter 122, transmit beamformer 121, probe/system, applications, and products (SAP) electronics 110, and a position sensor 112. The probe/SAP electronics 110 may be used to control the switching of the transducer elements 124. The probe/SAP electronics 110 may also be used to group transducer elements 124 into one or more sub-apertures.

The ultrasound probe 126 may be configured to acquire ultrasound data or information from the anatomical structures (e.g., organ, blood vessel, heart) of the patient based on the predetermined settings. Additionally, the ultrasound probe 126 may acquire position information (e.g., data), via the position sensor 112, that includes the spatial position, relative to a coordinate system and a reference point which may be predefined by the controller, of the probe 126. The position data may correspond to the acquired ultrasound image data, such that each image (or scanned image plane or frame) includes a corresponding position of the probe at the time the image data was acquired. The position data may be further indexed with one or more learned robot actions. For example, as a user moves the ultrasound probe 126 and adjusts an orientation of the probe or a probe pressure applied at an interface between the probe and an acquisition surface, feedback regarding the orientation and the probe pressure may be stored with a corresponding position of the probe such that the robot 144 may replicate the orientation and the probe pressure at the position during a future ultrasound acquisition without external force being provided by the user.

The ultrasound probe 126 is communicatively coupled to the controller 102 via the transmitter 122. The transmitter 122 transmits a signal to a transmit beamformer 121 based on acquisition settings received by the controller 102. The acquisition settings may define an amplitude, pulse width, frequency, gain setting, scan angle, power, time gain compensation (TGC), resolution, and/or the like of the ultrasonic pulses emitted by the transducer elements 124. The probe 126 may include an additional transmitter for transmitting the signals formed by the transmit beamformer 121. The transducer elements 124 emit pulsed ultrasonic signals into a patient (e.g., a body). The acquisition settings may be defined by the user utilizing the user interface 142. The signal transmitted by the transmitter 122 in turn drives a plurality of transducer elements 124 within a transducer array.

The transducer elements 124 emit pulsed ultrasonic signals into a body (e.g., patient) or volume corresponding to the acquisition settings along one or more scan planes. The ultrasonic signals may include, for example, one or more reference pulses, one or more pushing pulses (e.g., shear-waves), and/or one or more pulsed wave Doppler pulses. At least a portion of the pulsed ultrasonic signals back-scatter from the anatomical structures (e.g., heart, left ventricular outflow tract, breast tissues, liver tissues, cardiac tissues, prostate tissues, neonatal brain, embryo, abdomen, and the like) to produce echoes. The echoes are delayed in time and/or frequency according to a depth or movement, and are received by the transducer elements 124 within the transducer array of the probe 126. The ultrasonic signals may be used for imaging, for generating and/or tracking shear-waves, for measuring changes in position or velocity within the anatomic structure, differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored in memory 106, temporarily. The digitized signals correspond to the backscattered waves receives by each transducer element 124 at various times. After digitization, the signals still may preserve the amplitude, frequency, phase information of the backscatter waves. The receiver 128 may also transmit positional data, received from the position sensor 112 to the controller 102 and/or memory 106.

Optionally, the controller 102 may retrieve the digitized signals stored in the memory 106 to prepare for the beamformer processor 130. For example, the controller 102 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 106) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or apart of the controller. For example, the operations described being performed by the beamformer processor 130 may be configured to be performed by the controller 102.

The beamformer processor 130 performs beamforming on the digitized signals of transducer elements and outputs a radio frequency (RF) signal. The RF signal is then provided to an RF processor 132 that processes the RF signal. The RF processor 132 may include one or more processors. Optionally, the RF processor 132 may include a central controller circuit (CPU), one or more microprocessors, or any other electronic component capable of processing inputted data according to specific logical instructions. Additionally or alternatively, the RF processor 132 may execute instructions stored on a tangible and non-transitory computer readable medium (e.g., the memory 106). Optionally, the RF processor 132 may be integrated with and/or apart of the controller 102. For example, the operations described being performed by the RF processor 132 may be configured to be performed by the controller 102.

The RF processor 132 may generate different ultrasound image data types, e.g. B-mode, color Doppler (velocity/power/variance), tissue Doppler (velocity), and Doppler energy, for multiple scan planes or different scanning patterns based on the predetermined settings of the first model. For example, the RF processor 132 may generate tissue Doppler data for multi-scan planes. The RF processor 132 gathers the information (e.g. I/Q, B-mode, color Doppler, tissue Doppler, and Doppler energy information) related to multiple data slices and stores the data information, which may include time stamp and orientation/rotation information, in the memory 106.

Alternatively, the RF processor 132 may include a complex demodulator (not shown) that demodulates the RF signal to form IQ data pairs representative of the echo signals. The RF or IQ signal data may then be provided directly to the memory 106 for storage (e.g., temporary storage). Optionally, the output of the beamformer processor 130 may be passed directly to the controller 102.

The controller 102 may be configured to adjust the system settings, image presentation settings, and/or anatomical structures represented by the ultrasound data and/or ultrasound images acquired by the MDS 150. For example, the controller 102 may be configured to process the acquired ultrasound data (e.g., RF signal data or IQ data pairs) and prepare and/or generate frames of ultrasound image data representing the anatomical structure for display on the display 138. Acquired ultrasound data may be processed in real-time by the controller 102 during a scanning or therapy session as the echo signals are received. Additionally or alternatively, the ultrasound data may be stored temporarily in the memory 106 during a scanning session and processed in less than real-time in a live or off-line operation.

For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation.

The memory 106 may be used for storing processed frames of acquired ultrasound data that are not scheduled to be displayed immediately or to store post-processed images (e.g., shear-wave images, strain images), firmware or software corresponding to, for example, a graphical user interface, one or more default image display settings, programmed instructions, and/or the like. The memory 106 may store 2D and/or 3D ultrasound image data sets of the ultrasound data, where such 2D and/or 3D ultrasound image data sets are accessed to present 2D and 3D images. For example, a 2D or 3D ultrasound image data set may be mapped into the corresponding memory 106, as well as one or more reference planes. The processing of the ultrasound data, including the ultrasound image data sets, may be based in part on user inputs, for example, user selections received at the user interface 142.

The ultrasound imaging system of MDS 150 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 106 is of sufficient capacity to store at least several seconds worth of frames of ultrasound data. The frames of data are stored in a manner to facilitate retrieval thereof according to its order or time of acquisition. The memory 106 may comprise any known data storage medium. In one example, FIGS. 1A and 1B illustrate a system, comprising an ultrasound device comprising an ultrasound probe, a robot configured to couple to the ultrasound probe and a controller with computer-readable instructions stored on non-transitory memory thereof that when executed enable the controller to adjust the robot to a learning mode comprising a velocity control mode and a force control mode, the velocity control mode comprising translating a handle force of the ultrasound probe into a velocity command, the force control mode comprising estimating a probe force applied to an acquisition surface of a patient and adjust the robot to an image acquisition mode in response to an absence of an external force being applied to the ultrasound probe. By doing this, the robot may acquire an ultrasound image independently (e.g., without assistance and/or guidance from a user), which may increase time for the user to conduct other medical activities. Additionally, the robot may decrease variability between ultrasound image acquisitions due to different users (e.g., technicians) using different acquisition techniques. The robot may execute a single scan protocol for each scan protocol type, thereby allowing a user (e.g., a physician) to analyze consistent ultrasound images.

The learning mode further comprises learning one or more travel path profiles specific to an ultrasound scan type, wherein each travel path profile comprises a travel path, one or more velocities, one or more probe forces, and one or more probe orientations. As such, the robot may acquire ultrasound images from various scan planes at various probe forces while maintaining a desired acquisition rate.

The ultrasound scan type may be a scan type including one or more of organs, skeletal structures, vascular structures, and regions of a body. Each scan type comprises different travel path profiles. The image acquisition mode comprises executing the one or more travel path profiles learned in response to the absence of the external force and an input from a user for a selection of the ultrasound scan type. Thus, the robot may adjust starting and ending positions of the ultrasound probe similar to the positions used by the user during the training in order to acquire an ultrasound image closely resembling the ultrasound image acquired during the training.

In one example, the robot is a collaborative robot, the collaborative robot comprising at least one force sensor arranged at a hand, wherein the hand is configured to couple to the ultrasound probe. The force control mode during the learning mode comprises estimating the probe force applied by sensing an amount of motor actuation of one or more motors of the robot, wherein the amount of motor actuation is learned and replicated during the image acquisition mode. The handle force is a force applied to a handle of the ultrasound probe in a direction parallel to the acquisition surface, and wherein the probe force is a force applied at an interface between the ultrasound probe and the acquisition surface, wherein a direction of the probe force is angled to the acquisition surface. A force applied to the handle in a direction angled to the acquisition surface is not translated into the velocity command, wherein the velocity command is proportional to the handle force. In this way, the robot may be responsive to external pressures, such as external pressures applied by the user, a patient, or other source.

In various embodiments of the present invention, one or more components of MDS 150 may be included in a portable, handheld ultrasound imaging device. For example, display 138 and user interface 142 may be integrated into an exterior surface of the handheld ultrasound imaging device, which may further contain controller 102, beamformer processor 130, RF processor 132, and memory 106. Probe 106 may comprise a handheld probe in electronic communication with the handheld ultrasound imaging device to collect raw ultrasound data. Transmit beamformer 121, transmitter 122, and receiver 128 may be included in the same or different portions of the ultrasound imaging system 100. For example, transmit beamformer 121, transmitter 122, and receiver 128 may be included in the handheld ultrasound imaging device, the probe, and combinations thereof.

Turning now to FIG. 2A, it shows a high-level flow chart illustrating a method 200 for acquiring an ultrasound image via a user or a robot. Instructions for carrying out method 200 and the rest of the methods included herein may be executed by a controller based on instructions stored on a memory of the controller and in conjunction with signals received from sensors of the MDS system, such as the sensors described above with reference to FIGS. 1A and 1B. The controller may employ actuators of the MDS system to adjust operation different system components, according to the methods described below.

The method 200 begins at 203, which includes determining operating conditions and receiving user inputs. The operating conditions may include determining if a current ultrasound image is being acquired, if an ultrasound image is desired to be acquired, or if a user is actuating the ultrasound probe. User inputs may include a force against an acquisition surface and direction of movement of the probe, in one embodiment.

The method 200 proceeds to 206, which comprises determining if an anatomical region has been learned. The anatomical region may be learned in a previous teaching mode, wherein the user guides an ultrasound probe, to which a robot arm is coupled, across an anatomical region. The robot learns a travel path along with one or more pressures to apply along the general travel path to acquire an ultrasound image. The teaching mode is described in greater detail below with respect to FIGS. 3 and 4A.

If the anatomical region has not been learned, then the method 200 proceeds to 209, which comprises instructing the user to enter a velocity control mode. Instructing the user may include displaying an alert and/or a message on a display device. In one example, the display device may be a display device identical to the display device used to display an ultrasound image to the user in real-time. The velocity control mode may be a mode used during the training mode, as will be described in greater detail below.

If the anatomical region has been learned, then the method 200 proceeds to 212 to determine a desired reference position for a target organ and navigate an ultrasound probe to the desired reference position. In one example, the robot may automatically navigate the ultrasound probe to the desired reference position via feedback from the ultrasound machine (e.g., via position sensor feedback) and via learned forces and movements corresponding to the anatomical region desired to be scanned. Additionally or alternatively, the user may position the robot arm and ultrasound probe at the desired reference position without departing from the scope of the present disclosure, in one embodiment. Additionally or alternatively, the robot may actuate the arm and probe independently to the desired reference position to begin the ultrasound acquisition via feedback from a neural network, constructive network, open network, or the like via information from a position sensor of the probe along with information gathered during previous training modes.

The method 200 proceeds to 215, which includes receiving confirmation that the user and/or the robot has positioned the probe at the reference position, acquiring image data and position information from the probe, at the reference position, and calibrating the position sensor of the probe. In one example, the method at 215 may include receiving an input from the user (e.g., via the user interface) that the probe has been positioned at the desired reference position which may be based on a user selected scan protocol (e.g., a scan type, which may include a kidney scan, fetal scan, brain scan, heart scan, etc.). Additionally or alternatively, the method may include confirming the probe is at the reference position by acquiring image data and position information from the probe (e.g., via the transducer elements and the position sensor on the probe, respectively) and analyzing the acquired image data, at one or more image analysis models or frameworks (as discussed above with reference to the models stored in memory 106 in FIG. 1A). For example, the image data and/or images generated from the acquired image data, when the probe is positioned at the desired reference position, may be fed into one or more anatomical structure models, image recognition models, scan plane detection frameworks (e.g., algorithms), and the like. These models, frameworks, and/or algorithms, stored in the memory of the controller, may compare the acquired image or image data against stored images or image data and determine whether the acquired image matches anatomical landmarks/features of stored images at the reference position. If the controller determines, based on these models and/or algorithms that the ultrasound probe is at the desired reference position, the controller may store the corresponding image data (and/or generated image) and position data from the probe at the reference position. This position may then be stored as an origin of a coordinate system and all other positions of the probe (e.g., position data output by the position sensor on the probe) may be determined relative to this origin. In some embodiments, the reference position may additionally be determined/confirmed based on a-priori information, such as one or more inputs from the user received at 203. For example, the reference position may be determined based on an output of the probe, image data acquired at the reference position, and one or more user inputs. In this way, the position sensor of the probe, and the positional output of the sensor, is calibrated based on the predetermined reference position and image data acquired at that location and, in some embodiments, user inputs. The reference position described above is used as a landmark for calibrating the algorithms, models, and frameworks described herein. In some embodiments, additional landmark positions may be beneficial and provide additional information for increasing the accuracy of the models/algorithms/frameworks. For example, at 215, the method may include prompting the user to navigate to a single reference position, wherein image data gathered at the reference position may allow the robot to determine a desired scan protocol and/or a desired scan type without further input from the user.

The method proceeds to 218 to initialize the algorithms and models according to a selected scan protocol. A scan protocol may include a list of the images and measurements that are to be acquired during a specified ultrasound examination (e.g., procedure). The list of images may include specified scan planes at certain organs or anatomical landmarks. For example, the list may include a particular plane (e.g., scan plane) within the organ or anatomical feature that contains the desired view. Each protocol may include a plurality of these desired views or images and corresponding measurements to be taken. Each item in the scan protocol may utilize individual models and algorithms (e.g., first item head, second item heart). Thus, before starting a scan protocol item, the method at 218 may include selecting the appropriate general travel paths that correspond to the anatomical part to be scanned in the scan protocol type. In one example, the selected scan protocol may be selected by the user, wherein the user selects a desired scan type (e.g., kidney scan) and wherein the selected scan type is associated with a plurality of scan images comprising a plurality of probe travel paths.

The method 200 proceeds to 221, which includes executing the robotic image acquisition. The robotic image acquisition may occur in response to the ultrasound probe being free of external forces other than a force provided by the robot. As such, the user may no longer be applying a force to the ultrasound probe. During the robotic image acquisition, the hand of the user may be removed from the robot arm such that the user no longer applies a force to the robot arm. In response, the robot may begin to scan a general travel path with one or more pressures at 224. Each of the general travel path and the one or more pressures may be learned during a previous training mode, wherein the user guided the robot arm along the general path to acquire desired ultrasound images for an anatomical region. While acquiring the ultrasound images along the general path, the robot may apply one or more pressures along an axis perpendicular to a scanning surface (e.g., a patient's skin). The one or more pressure may correspond to pressures previously learned during training mode.

Additionally or alternatively the one or more forces applied by the robot against an acquisition surface via the ultrasound probe may be based on forces previously learned. However, the one or more forces may deviate from the previous forces learned. For example, as the robot arm progresses along the general path, a plurality of ultrasound images may be acquired and compared to previously acquired images associated with the scan protocol of the desired anatomical region. However, the robot may adjust forces applied along the general path to increase a matching between currently acquired images and previously acquired images. In this way, pressures applied by the robot via the robot arm may be within a pressure range to acquire the desired ultrasound images. In one example, the pressure range may be 1 N to 45 N, wherein 1 N may correspond to a lower threshold pressure capable of acquiring a desired ultrasound image and 45 N may correspond to an upper threshold pressure capable of acquiring an ultrasound image. However, other pressure ranges have been contemplated. Several factors, such as patient physiology (e.g., pressure sensitivity), robotic constraints, etc., may be taken into account when determining the upper pressure threshold. It will be appreciated that the threshold pressure range may include other pressure values without departing from the scope of the present disclosure. For example, the threshold pressure range may be between 2.5 N to 30 N, 3 N to 25 N, 5 N to 20 N, or another similar range. By allowing the robot to dynamically adjust forces applied via the ultrasound probe to the acquisition surface, the robot may adjust a scan protocol in real-time to improve an ultrasound image quality and matching to previously acquired ultrasound images.

In one embodiment, the probe pressure applied by the robot to the acquisition surface may be increased relative to a learned probe pressure due to a patient body fat being higher than a body fat of the patient with which the probe pressure was learned. Due to the increased amount of fat distorting the gathered ultrasound image, the robot may increase the probe pressure to displace fat between the probe and the target organ to improve an image quality. By improving the image quality, the ultrasound image of the target structure may comprise a higher resolution, fewer artifacts, or other image irregularities generated due to fat obstructing the ultrasound probe.

Additionally or alternatively, the robot may not deviate from previous learned forces, in one embodiment. As such, the user may train the robot with a variety of patient body shapes and sizes such that the robot may learn forces corresponding to various levels of the body fat for a single scan protocol.

The method 200 proceeds to 227 to determine if the robot image acquisition is interrupted. The image may be interrupted if the user applies an external pressure to the robot arm. The robot arm may be disabled in response to the external pressure from the user such that the robot arm no longer applies a pressure to the ultrasound probe to guide it along the general path or a pressure to the ultrasound probe to press against the image acquisition surface.

If the image is interrupted, then the method 200 proceeds to 230 to disable the robotic image acquisition. As described above, the robot no longer applies forces against the ultrasound probe, against the image acquisition surface, or along the image acquisition surface.

The method 200 proceeds to 233 and enters the velocity control mode. In the velocity control mode, the robot may follow a handle force applied by the user to a handle of the ultrasound probe. The robot may increase a velocity in a direction based on an increased handle force in the direction. Conversely, the robot may decrease a velocity in a direction based on a decreased handle force in the direction. As such, the robot may proportionally adjust a velocity in a direction based on a handle force and direction of force. The velocity control mode is described in greater detail with respect to FIGS. 3 and 4A.

If the image is not interrupted, then the method 200 proceeds to 236 to determine if the scan protocol is complete. The scan protocol may be complete when the robot determines that each of the desired scans of each of the travel paths of the scan protocol of the anatomical location has been acquired. Additionally or alternatively, the user may confirm completion of the scan protocol. In one example, the confirmation may include the user selecting an affirmative response indicating the desired scans have been acquired and match previously acquired scans of the anatomical region such that the user may perform a medical diagnosis.

If the scan protocol is complete and confirmed by the user, then the method 200 proceeds to 239 to disable the robotic image acquisition, similar to 230 previously described. In this way, the robot acquired one or more ultrasound images of the desired anatomical region from a beginning of the image acquisition to an end of the image acquisition without human intervention and other external forces. In this way, the user (e.g., a medical professional) may conduct other medical tasks such as writing notes, evaluating other patients, or the like.

If the scan protocol is not complete, then the method 200 proceeds to 242 which includes determining one or more travel paths to be captured and/or recapture. In one example, the ultrasound device may automatically determine the one or more travel paths that are desired to be acquired and/or reacquired. If images from a travel path still have not been acquired, then the ultrasound device may determine than one or more ultrasound images corresponding to the travel path have not been acquired. As such, the robot may be instructed to begin acquiring scan images along the travel path. Additionally or alternatively, the user may select one or more acquired scan images and indicate a request to reacquire the selected images. Additionally or alternatively, the ultrasound device may automatically determine and select one or more acquired scan images as being mismatched with scanned images from a previous training session from which the robot learned the one or more travel paths. The ultrasound device may then automatically signal to reacquire the one or more selected images.

The method 200 proceeds to 245, which includes determining if the one or more travel paths are learned. If the one or more travel paths are learned, then the method 200 proceeds to 248, which includes continuing the robotic image acquisition of the selected travel paths. In this way, the robot may automatically begin reacquiring one or more scan images along one or more general travel paths.

If the travel paths are not learned, then the method 200 proceeds to 251 to enter the velocity control mode. The velocity control and training of the robot will be described in greater detail herein. By training the robot, the robot may learn one or more travel paths corresponding a unique scan protocol. The robot may learn forces and velocities applied along the travel path such that images acquired during a future scan protocol without the assistance of a user may match images acquired during the robot training under the guidance and/or assistance of the user.

Turning now to FIG. 3, it shows a method 300 for training the robot to acquire one or more ultrasound images of a scan protocol corresponding to an anatomical region. The scan protocol may comprise one or more travel paths, each comprising a general path profile along which an ultrasound probe and robot arm are actuated.

The method 300 begins at 302, which comprises receiving a user input regarding one or more anatomical locations to be scanned. In one example, the one or more anatomical locations may correspond to a scan protocol for an ultrasound image acquisition of a single, target organ. However, due to the proximity of organs relative to one another, multiple ultrasound images may be acquired from multiple angles and anatomical locations to acquire a complete image of the target organ. The user input may include the user inputting to the ultrasound device an anatomical location to be acquired, wherein the anatomical region may include one or more of a fetus, a kidney, a liver, and the like. Additionally or alternatively, the user input may include actuating a probe and a robot arm coupled to the probe to the anatomical location. The anatomical location may be scanned, wherein the scan may be stored and indexed as a starting point for a travel path of a scan protocol. By automatically determining the starting point, it may reduce a number of tasks prompted for the user to execute to train the robot, thereby increasing an efficiency of the robot training.

Thus, in one example, the user may actuate the robot arm, which is coupled to (e.g., grasping and/or holding and/or clamping) the ultrasound probe, to the anatomical region at which the scan protocol may begin. The anatomical region may be automatically learned and stored in memory based on feedback from one or more of a position sensor of the ultrasound device and image feedback from the ultrasound probe.

The method 300 proceeds to 305, which comprises adjusting the robot to a velocity control mode. In the velocity control mode, the robot may sense all external forces applied to the ultrasound probe and to an image acquisition surface. In one example, the robot does not contribute to the probe force, wherein the probe force corresponds to a force applied at an interface between the probe and the acquisition surface (e.g., the patient's skin). As such, the robot may estimate an amount of force applied at the acquisition surface by measuring an amount of motor actuation of an actuator of the robot, wherein the amount of motor actuation may be proportional to a desired probe force generated by the user. The velocity control mode may further comprise tracking and learning forces, positions, and orientations of the probe over time. In one example, the velocity control mode learns a trajectory in which to actuate the probe with a plurality of forces, positions, and orientations included along the trajectory. In the velocity control mode, the robot assists the user in guiding the ultrasound probe in response to handle forces and a direction of the handle forces. In one example, if handle force applied by the user increases in a direction, then the robot assistance also increases in the same direction.

The method 300 proceeds to 308, which includes learning a first travel path and a first pressure applied along a path profile (e.g., a trajectory) while in the velocity control mode. The path profile may comprise general path along which the ultrasound probe, and the robot arm, are actuated. The first travel path may be learned as a general path due to variances between patient anatomies due to one or more of body fat, height, bone structure, muscle mass, organ location, and the like. By learning the travel path as a general path, the robot may learn a range with which to actuate the probe along a three-dimensional direction. By doing this, an accuracy of ultrasound images gathered for a patient population via the robot may be increased. While in the velocity control mode, the robot may assist the user to move the probe in a sensed desired direction, in one embodiment. As such, the user may provide a motive power, wherein the robot may provide a computer-control of a motion generated in a shared direction with the user. The motive power provided by the user may be sensed at an ultrasound probe handle and may be in a direction parallel to an acquisition surface. Forces angled or perpendicular to the acquisition surface may not be interpreted by the robot as a request from the user to move in a desired location but as an adjustment in probe force and/or orientation and are therefore learned.

Thus, the robot, while in the velocity control mode and undergoing the learning, may comprise a velocity based on a user handle force. In one example, the user may apply a handle force to a handle of the ultrasound probe, wherein the handle force is applied in a direction parallel to an acquisition surface (e.g., a patient's skin). The robot may translate the handle force into a velocity proportional to the handle force, wherein the velocity increases as the handle force increases. However, the robot may not assist the user in applying a probe pressure to the acquisition surface while in the force control mode during the training.

As the robot arm and the ultrasound as actuated along the first travel path, the robot may learn various positions along the travel path, wherein the various positions may be indexed with one or more of feedback from a position sensor of the ultrasound device and one or more images gathered at each of the various positions. As such, a first position may be indexed with a first image and feedback from the position sensor corresponding to the first position. A second position may be indexed with a second image and feedback from the position sensor corresponding to the second position. Force applied along each of the positions and travel paths may be estimated via an amount of motor (e.g., actuator) actuation of the robot.

Once the first travel path is learned, the method 300 proceeds to 317, which includes determining if there are additional travel paths to learn. In one example, the user may indicate via the user interface that there are additional travel paths included in the scan protocol for the anatomical region. Additionally or alternatively, in one embodiment, the ultrasound machine may determine that the scan protocol comprises additional travel paths to learn in response to the user lifting the probe away from the acquisition surface for a threshold amount of time (e.g., greater than 3 seconds) before returning and pressing the probe against the acquisition surface at a location different than the positions along the first travel path. Additionally or alternatively, if the probe is moved away from the acquisition surface and placed on a portion of the acquisition surface different than a location from which it was just removed, then it may be determined a new travel path is being trained.

If there are additional travel paths, then the method 300 proceeds to 320 to learn n travel paths and m pressures applied. In one example, n is less than or equal to m, such that there may be more pressures learned than travel paths. In one embodiment, the travel paths and pressures may be learned and stored sequentially such that when the robot executes the scan protocol independently, the robot conducts the first travel path first, the second travel path second, the third travel path third, and so on in an order identical to the order learned. Additionally or alternatively, in one embodiment, the robot may execute the travel paths in an order different than the order learned, wherein the robot executes a third travel path first, a seventh travel path second, and so on.

Once the travel paths of the scan protocol are learned, the method 300 proceeds to 323 to determine if the image is confirmed. The image may correspond to a combined image of the plurality of ultrasound scan images acquired while scanning the plurality of travel paths, wherein the images are combined to provide a complete view of a target organ and/or an anatomical region. In one example, the user may review the image and provide a user input, via the user interface, indicating the image is not complete or does not provide a sufficient depiction of the target anatomical area to perform a medical evaluation. In such an example, the method 300 proceeds to 326 to relearn one or more travel paths. Additionally or alternatively, in one embodiment, the method may include learning one or more additional travel paths. In such an example, the user may forget a travel path corresponding to the scan protocol, wherein upon reviewing the final image, the user realizes one or more forgotten travel paths. As such, the user may update the scan protocol with the missing paths by actuating the ultrasound probe to which the robot arm is clamped as described above.

If the image is confirmed, then the method 300 proceeds to 329, which includes storing the identified image and setting the scan protocol for the anatomical region. Storing the image may include storing the classified image (e.g., including a name of the target plane and/or anatomical structure and/or starting point of the first travel path) and any associated measurements taken for that image, including the plurality of ultrasound images and position data.

In one embodiment, the methods of FIGS. 2A, 2B, and 3 illustrate a method for learning a travel path profile and one or more pressures applied along the travel path profile in response to an external handle force and acquiring an ultrasound image along the travel path profile by applying one or more forces against an acquisition surface of a patient via a robot without the external handle force. The external handle force may be applied by a user. During the acquiring, applying one or more forces against the acquisition surface is performed via only the robot. The learning further comprises entering a velocity control mode, the velocity control mode comprising learning the external handle force as a velocity to move the ultrasound probe along the acquisition surface. The learning further comprises a probe force, wherein the probe force is applied by a user and measured along an axis angled to the acquisition surface, and wherein the velocity is learned via forces applied to a handle of the ultrasound probe in a direction parallel to the acquisition surface. The robot does not contribute to the probe force during the learning, and wherein the robot contributes to the handle force during the learning. The acquiring further comprises applying the probe force via only a robot force, the robot force being equal to the probe force learned during the learning. In one example, pressures corresponding to the probe forces are between 1 and 60 N. In such an example, the probe forces may be applied at different locations and orientations of the travel path profile. Furthermore, the learning comprises learning the pressures applied at the different locations and orientations of the travel path profile, which may improve an accuracy of the ultrasound image acquired by only the robot. The travel path profile is one travel path profile of a plurality of travel path profiles corresponding to a scan protocol type, wherein the scan protocol type corresponds to a scan sequence for a desired anatomical region. By relating each travel path to a specific scan protocol type, the robot may increase its independence from the user, such that the robot may automatically determine a scan protocol type based on a starting portion of a travel path, for example.

Turning now to FIG. 4A, it shows an embodiment of an ultrasound system 400 being used to acquire an ultrasound image of a patient 410. In the example of FIG. 4A, a robot 420 is being trained by a user 430. In one example, the robot 420 is a collaborative robot and the user is a medical professional, such as a physician, physician's assistant, ultrasound technician, nurse practitioner, and the like. In the example of FIG. 4A, the robot 420 is a velocity control mode as the user 430 is training the robot 420.

The robot 420 comprises an arm 422. The arm 422 may comprise one or more joints, wherein each joint may comprise a three-axis force gauge 426 configured to execute force measurements along with a force sensor 424. A force sensor 424 is illustrated at a hand 428 of the robot 420.

As shown, the hand 428 may couple to a probe 402 of the ultrasound system 400. The hand 428 may grasp, clamp, wrap around, and/or grab the probe 402. In one embodiment, the hand 428 may be coupled to the probe 402 via magnetism, a fastening device (e.g., a screw, bolt), and/or an adhesive (e.g., tape, glue, Velcro, etc.). Additionally or alternatively, the hand 428 is integrally formed with the ultrasound probe 402 such that the hand 428 and the probe 402 are one piece.

The probe 402 is pressed against an acquisition surface 412 of the patient 410. In the example of FIG. 4A, in the training mode the robot 420 may not apply forces along the y-axis or along an axis angled to the acquisition surface 412. As such, forces pressing the probe 402 against the acquisition surface 412, resulting in the probe force at the interface between the probe and the acquisition surface 412, may be solely provided by the user 430. Additionally or alternatively, the robot may not assist in adjusting an orientation of the probe 402.

Said another way, a proportional-integral-derivative (PID) controller 404 executed via a computer (e.g., controller 102 of FIGS. 1A and 1B). The PID controller 404 may be a three-term controller using feedback loops wherein it calculates an error values between a desired value and a measured value and determines a correction based on a proportional term, an integral term, and a derivative term. The PID controller 404 may execute the velocity control mode via the velocity control 408, which allows the robot 420 to apply a desired velocity to the probe 402. This may include input from the handle force, which may be a three-axis handle force, wherein forces along the y-axis may not contribute to a desired velocity input. That is to say, handle forces applied along the y-axis (e.g., angled to or perpendicular to the acquisition surface) may not be used to determine the desired velocity which is proportional to the handle forces. During the velocity control, the desired velocity and the measured velocity may be compared and their difference may be provided to the PID controller 404 as the input delivered to the robot 420 via the velocity control 408.

In one example, as the user 430 actuates the probe 402 along the acquisition surface 412 via various forces with a portion of the force applied parallel to the y-axis, the force sensors of the robot 420 may provide feedback to the controller, wherein the forces along a travel path and/or within a fixed position of the travel path are learned and included in a travel path profile (e.g., a trajectory), as described above. In one example, the forces may be estimated based on an amount of motor actuation of a motor of the robot 420 (e.g., arm 422, motor in a joint, etc.). More specifically, the probe forces 407 may be estimated and learned as forces, positions, and orientations applied over time 409 of the probe along the travel path and/or a general trajectory. The position and orientation may be estimated via feedback from the position sensor of the ultrasound device along with feedback from the motors (e.g., actuators) of the robot 420. In this way, the probe forces may be learned as various orientations and forces to apply to the acquisition surface at various time points and positions along a single travel path.

The handle pressure and/or the handle force may be learned as a velocity with which to actuate the probe 402 along the travel path. The velocity control mode may function via assisting the user in actuating the ultrasound probe 402 in a desired direction along the x-z plane. For example, handle forces applied by the user's hand 432 to the probe 402 may be estimated and converted into a desired velocity. The PID 404 may signal to the velocity control mode 408 to signal to the robot 420 a velocity command in a direction the user 430 is applying the force along the x-y plane. The robot 420 may begin to apply a pressure to the probe handle in combination with the pressure applied by the user's hand 432 to actuate the probe in a desired direction parallel to the acquisition surface. As the handle forces applied by the user's hand increase, the velocity in which the robot actuates the probe 402 also increases. As the handle forces decrease, the velocity in which the robot 420 actuates the probe 402 also decreases. As such, probe forces are not included in the velocity control mode sensing. Said another way, force perpendicular or angled to the acquisition surface 412 are not included in the velocity command.

In one embodiment, additionally or alternatively, the robot 420 may learn a range of velocities and forces along the travel path such that the travel path profile comprises upper and lower velocity limits and upper and lower force limits, wherein the robot 420 may guide the probe with the upper and lower limits of these velocities and forces to acquire a desired ultrasound image. As such, the robot 420 may not exceed or fall below velocities and forces learned from the user 430.

As such, in the example of FIG. 4A, during the training, the user 430 guides the probe 402 to acquire an ultrasound image 452. The ultrasound image 452 is displayed to the user 430 on a display device 454 to allow the user to adjust a position of the probe 402 to acquire desired scans along various travel paths and various probe orientations and probe pressures. As the user 430 acquires the image 452, the robot 420 may assist the user 430 in guiding the probe 402 along direction parallel to the acquisition surface 412. While doing this, the robot 420 may provide feedback regarding probe velocities parallel to the acquisition surface 412 and probe forces angled to the acquisition surface. The velocities, forces, orientations, and positions may be learned and stored in memory, wherein instructions stored in memory may be executed and enable the controller to signal to the robot to acquire ultrasound images via the learned velocities and forces.

Turning now to FIG. 4B, it shows an embodiment 450 of the ultrasound system 400 acquiring the ultrasound image 452, which is displayed on the display device 454, via the robot 420. The user may select a scan protocol, such as a fetal scan, kidney scan, liver scan, etc. and the robot 420 may actuate the probe 402 to a desired location on the acquisition surface 412. The robot 420 may begin to acquire ultrasound images, which may be projected onto the display device 454 in real-time. In the examples of FIGS. 4A and 4B, the ultrasound image 452 is a fetal image, wherein forces and velocities implemented via the robot 420 to acquire the ultrasound image 452 are substantially identical to those learned in the example of FIG. 4A.

In one example, the robot 420 may comprise a three-degrees of freedom translation stage. Furthermore, the force sensor 424 may be a six-axis force/torque sensor mounted between the hand 428 and the probe 402 to measure probe-tissue contact forces (e.g., the probe force at the interface between the probe and the acquisition surface). An end effector of the robot 420 may be the ultrasound probe 402 used to visualize a target of interest.

The PID controller 404 may control probe forces along the y-axis by implementing force control 405 and control velocities via a trajectory control 406. In one example, the trajectory control 406 comprises guiding the ultrasound probe 402 via the robot 420 along a general travel path. The general travel path may correspond to a learned travel path, however, due to patient variability as described above along with patient movement, the general travel path may comprise a starting position and an end position and a plurality of scan positions therebetween. Following the general travel path may allow the robot 420 to actuate the probe to each of the starting position, the plurality of scan positions, and the end position of the learned travel path despite variances between patients. Additionally or alternatively, in one embodiment, the general travel path may comprise a general travel path total length, wherein the total length may only include distance traveled parallel to the acquisition surface. As such, distances traveled angled to the acquisition surface may not be included in the general travel path total length. Additionally or alternatively, the trajectory control 406 may guide the robot 420 along the general travel path, which may be within a threshold range of the learned travel path, while also guiding an orientation and a position of the probe along the general travel path. The force control 405 may signal a force to apply to the acquisition surface 412 at each of the orientation and the position.

In one example, threshold range of the general travel path includes signaling to the robot 420 to guide the probe 402 within a percentage of the learned travel path. In one example, the percentage is within 80%, additionally or alternatively, the percentage is within 90% of the learned travel path. The percentage may be adjusted based on a variety of parameters including scan type, patient shape, anatomical region, and the like.

A force error may be a function of time as illustrated below in equation 1:

$$e(t) = F_d - F_m \qquad \text{Equation 1;}$$

$F_d$ may be a desired force and $F_m$ may be a measured force. A difference between the desired force and the measured force may be translated into a velocity input, u(t), in one example. In one embodiment, the velocity command signaled to the robot 420 is an estimation of a sum of the user velocity input and the robot velocity input during the learning mode. Said another way, the PID controller 404 may estimate the user contribution to the velocity input during the training mode such that a total velocity during the training mode is used as the velocity command during the image acquisition via only the robot in the absence of the external force. The force control 405 may be substantially identical to the estimated probe forces learned during the training mode. As such, motors and actuators of the robot 420 may be commanded to similar positions sensed during the training mode to mimic the forces and orientations performed by the user.

In one example, the trajectory control 406 is prioritized over the force control 405. As such, the PID 404 may prioritize maintaining the probe 402 along the general travel path as opposed to maintaining a desired pressure. However, the PID 404 and the force control 405 may still maintain the probe pressure within a desired range, wherein the desired range is between the highest and lowest pressures learned during the training.

In one example, additionally or alternatively, to begin the ultrasound image acquisition via only the robot 420, a user, such as the user 430 of FIG. 4A, may set the probe 402 on the acquisition surface 412, wherein the robot 420 may automatically identify the scan protocol based on the placement of the probe 402. For example, each of the various different scan protocols may comprise different travel path profiles, wherein the different travel path profiles may comprise different starting locations on the acquisition surface 412. As such, the robot 420 may associate the placement of the ultrasound probe 402 with a specific travel path profile, wherein the travel path profile may be linked to one scan protocol. In one embodiment, if the travel path profile corresponds to multiple scan protocols, then the user may be requested to provide input as to which scan protocol is desired. In response to being arranged on the acquisition surface 412 (e.g., the patient's skin), the trajectory control 406 and the force control 405 may begin to signal to the robot 420 via the PID 404 to actuate the probe along the general travel path with a desired orientation, position, and force applied over time.

The user may disable the robot 420 from acquiring the ultrasound image 452 by applying an external force to the ultrasound probe 402. In one example, this may include applying a handle force. In response, the PID controller 404 may signal the robot 420 to stop applying forces to the acquisition surface via the force control and to enter the velocity control mode, wherein the robot 420 may assist the user in actuating the probe in a desired direction. Thus, if an external force is applied to the ultrasound probe 402, image acquisition guided via the robot 420 is terminated and the robot 420 no longer applies a probe force angled to the acquisition surface 412.

In one aspect, a medical imaging device, such as an ultrasound device, is configured to merge two images of a reference point. The images may be acquired from disparate vantage points relative to a patient's body. The technical effect of merging the two images of the reference point is to provide a single, combined image of the reference point for medical analysis with a high degree of accuracy to accurately diagnose a condition of the patient.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   defining an anatomical structure model using machine learning to identify one or more anatomical structures of interest;
   learning a travel path profile to a structure of interest of the one or more anatomical structures of interest and one or more pressures applied along the travel path profile in response to an external handle force directly applied to a probe handle of a probe via a user;
   receiving confirmation that a correct ultrasound image has been acquired;
   setting a scan protocol for an anatomical region; and
   acquiring an ultrasound image along the travel path profile by applying one or more forces against an acquisition surface of a patient via a robot without the external handle force;
   wherein the travel path profile is one travel path profile of a plurality of travel path profiles corresponding to a scan protocol type, wherein the plurality of travel path profiles in the scan protocol are executed in an order different than the order learned.

2. The method of claim 1, wherein the external handle force is applied by the user, and wherein the applying one or more forces against the acquisition surface is performed via only the robot.

3. The method of claim 1, wherein the learning further comprises entering a velocity control mode, the velocity control mode comprising learning the external handle force as a velocity to move the probe along the acquisition surface.

4. The method of claim 3, wherein the learning further comprises a probe force, wherein the probe force is applied by the user and measured along an axis angled to the acquisition surface, and wherein the velocity is learned via force applied to the probe handle of the probe in a direction parallel to the acquisition surface.

5. The method of claim 4, wherein the acquiring further comprises applying the probe force via only a robot force, the robot force being equal to the probe force learned during the learning.

6. The method of claim 1, wherein one or more pressures are between 1 and 45 N, and wherein one or more pressures are applied at different locations and orientations of the travel path profile, and wherein the learning comprises learning the pressures applied at the different locations and orientations of the travel path profile, comparing the ultrasound image to previously acquired ultrasound images and dynamically adjusting the pressures applied in real-time to improve image quality.

7. A system, comprising:
   an ultrasound device comprising an ultrasound probe;
   a robot comprising an arm configured to couple to the ultrasound probe; and
   a controller with computer-readable instructions stored on non-transitory memory thereof that when executed enable the controller to:
   adjust the robot to a learning mode to learn a travel path profile to a structure of interest;
   wherein the learning mode comprises a velocity control mode, the velocity control mode comprising translating a handle force of the ultrasound probe into a velocity command, wherein the handle force comprises an external force directly applied to a handle of the ultrasound probe via a user's hand;
   instruct the robot via a proportional-integral-derivative controller to actuate the ultrasound probe along an x-y plane, wherein the robot applies a pressure to the ultrasound probe in combination with the pressure applied by the user's hand;
   disable the robot from acquiring an ultrasound image when the handle force is applied;
   adjust the robot to an image acquisition mode in response to an absence of the external force being applied to the ultrasound probe; and
   acquire the ultrasound image along a travel path, wherein the travel path profile is one travel path profile of a plurality of travel path profiles corresponding to a scan protocol type, wherein the plurality of travel path profiles in a scan protocol are executed in an order different than the order learned.

8. The system of claim 7, wherein each travel path profile of the plurality of travel path profiles comprises a travel path, one or more velocities, one or more probe forces, and one or more probe orientations.

9. The system of claim 8, wherein the image acquisition mode comprises executing the travel path profiles learned in response to the absence of the external force and an input from the user for a selection of the ultrasound scan type.

10. The system of claim 8, wherein the scan protocol is a scan type including one or more of organs, skeletal structures, vascular structures, and regions of a body.

11. The system of claim 10, wherein each scan type comprises different travel path profiles.

12. The system of claim 7, wherein the robot is a collaborative robot, the collaborative robot comprising at least one force sensor.

13. The system of claim 7, wherein probes forces sensed during the learning mode comprises estimating a probe force applied by sensing an amount of motor actuation of one or more motors of the robot, wherein the amount of motor actuation is learned and replicated during the image acquisition mode.

14. The system of claim 13, wherein the handle force is in a direction parallel to an acquisition surface, and wherein the probe force is a force applied at an interface between the ultrasound probe and the acquisition surface.

15. The system of claim 14, wherein a force applied to the handle in a direction angled to the acquisition surface is not translated into the velocity command, wherein the velocity command is proportional to the handle force.

16. A method for acquiring an ultrasound image, comprising:
   learning a plurality of travel path profiles, each travel path profile comprising a travel path, one or more velocities, one or more probe forces, and one or more orientations, wherein the learning is in response to an external force being applied by a user's hand directly to a handle of an ultrasound probe to which a hand of a robot is coupled, wherein one or more velocities are learned via measurements taken by a force sensor and a force gauge based on a handle force and wherein one or more probe forces and one or more orientations are learned based on probe forces applied angled to an acquisition surface of a patient; and
   acquiring the ultrasound image via only the robot in response to the external force being absent, wherein the robot is signaled to execute one or more velocities, one or more probe forces, and one or more orientations learned along the plurality of travel path profiles, wherein the ultrasound image is acquired from a travel path of the plurality of travel path profiles corresponding to a scan protocol type, wherein the plurality of travel path profiles in the scan protocol are executed in an order different than the order learned;
   wherein at least one of the probe forces is dynamically adjusted relative to the learned pressure based on patient body type.

17. The method of acquiring the ultrasound image of claim 16, wherein acquiring the ultrasound image is terminated in response to a presence of the external force.

18. The method of acquiring the ultrasound image of claim 16, wherein acquiring the ultrasound image via only the robot further includes an input from a user indicating a desired scan protocol type, and wherein the robot actuates the ultrasound probe to a starting position on the acquisition surface based on the desired scan protocol type.

* * * * *